(12) United States Patent
Maeda et al.

(10) Patent No.: US 12,296,092 B2
(45) Date of Patent: May 13, 2025

(54) CPAP DEVICE

(71) Applicant: Murata Manufacturing Co., Ltd., Kyoto (JP)

(72) Inventors: Hiroki Maeda, Kyoto (JP); Yoshihide Amagai, Kyoto (JP); Yoshio Yamanaka, Kyoto (JP); Yoshitaka Hane, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 677 days.

(21) Appl. No.: 17/647,638

(22) Filed: Jan. 11, 2022

(65) Prior Publication Data

US 2022/0134037 A1 May 5, 2022

Related U.S. Application Data

(63) Continuation of application No. PCT/JP2020/020720, filed on May 26, 2020.

(30) Foreign Application Priority Data

Jul. 12, 2019 (JP) ................................. 2019-129750

(51) Int. Cl.
*A61M 16/00* (2006.01)
*A61M 16/06* (2006.01)
*A61M 16/08* (2006.01)

(52) U.S. Cl.
CPC ...... *A61M 16/0066* (2013.01); *A61M 16/022* (2017.08); *A61M 16/06* (2013.01);
(Continued)

(58) Field of Classification Search
CPC .......... A61M 16/0057; A61M 16/0066; A61M 16/021; A61M 16/022; A61M 16/024;
(Continued)

(56) References Cited

U.S. PATENT DOCUMENTS

| 2001/0017134 | A1 | 8/2001 | Bahr |
| 2003/0236015 | A1* | 12/2003 | Edirisuriya ........... A61M 16/16 439/191 |

(Continued)

FOREIGN PATENT DOCUMENTS

| JP | 2001-276223 A | 10/2001 |
| JP | 2003-506161 A | 2/2003 |

(Continued)

OTHER PUBLICATIONS

International Search Report for PCT/JP2020/020720 dated Aug. 11, 2020.
Written Opinion for PCT/JP2020/020720 dated Aug. 11, 2020.

*Primary Examiner* — Joseph D. Boecker
(74) *Attorney, Agent, or Firm* — McDonald Hopkins LLC

(57) ABSTRACT

The present disclosure relates to a continuous positive airway pressure (CPAP) device which sends, into an airway of a user, air sucked into the device. A body unit as a first unit has a cylindrical first lead-out portion through which air circulates. A base unit as a second unit has a third introduction portion to which the first lead-out portion is to be connected. A body-side terminal is provided as a first terminal with conductivity at the first lead-out portion of the body unit. A base-side terminal is provided as a second terminal with conductivity at the third introduction portion of the base unit. The body-side terminal is in contact with the base-side terminal while the body unit is attached to the base unit.

9 Claims, 10 Drawing Sheets

(52) U.S. Cl.
CPC ... *A61M 16/0816* (2013.01); *A61M 2205/121* (2013.01); *A61M 2205/14* (2013.01); *A61M 2205/587* (2013.01); *A61M 2205/8206* (2013.01)

(58) Field of Classification Search
CPC .......... A61M 16/0069; A61M 16/0816; A61M 16/109; A61M 16/16; A61M 2205/121; A61M 2205/14; A61M 2205/587; A61M 2205/8206; A62B 18/006; A62B 18/045
See application file for complete search history.

(56) References Cited

U.S. PATENT DOCUMENTS

| | | | |
|---|---|---|---|
| 2006/0191531 A1* | 8/2006 | Mayer | A61M 16/0066 128/200.11 |
| 2008/0000474 A1 | 1/2008 | Jochle et al. | |
| 2010/0147301 A1* | 6/2010 | Kwok | A61M 16/0875 128/204.21 |
| 2011/0308518 A1 | 12/2011 | McGroary et al. | |
| 2013/0239960 A1* | 9/2013 | Bertinetti | E05B 17/2057 128/202.22 |
| 2015/0306332 A1* | 10/2015 | Bafile | A61M 16/1095 128/202.27 |
| 2016/0310689 A1* | 10/2016 | Osborne | A61M 16/1085 |
| 2018/0185606 A1* | 7/2018 | Van Schalkwyk | A61M 16/1095 |
| 2020/0330720 A1* | 10/2020 | Formica | A61M 16/0816 |

FOREIGN PATENT DOCUMENTS

| | | |
|---|---|---|
| JP | 2008-517682 A1 | 5/2008 |
| JP | 2012-517850 A1 | 8/2012 |
| JP | 2017-500126 A1 | 1/2017 |

* cited by examiner

//fit
CPAP DEVICE

CROSS REFERENCE TO RELATED APPLICATION

This is a continuation of International Application No. PCT/JP2020/020720 filed on May 26, 2020 which claims priority from Japanese Patent Application No. 2019-129750 filed on Jul. 12, 2019. The contents of these applications are incorporated herein by reference in their entireties.

BACKGROUND ART

Technical Field

The present disclosure relates to a continuous positive airway pressure (CPAP) device which sends, into an airway of a user, air sucked into the device.

A continuous positive airway pressure device as described in Patent Document 1, that is, a so-called CPAP device is used for sleep-related treatment for, for example, obstructive sleep apnea syndrome (OSA) to supply fluid to a user. The CPAP device is a device which has a blower with a built-in fan and supplies fluid from the blower to a mask worn over a mouth and a nose by a user at a pressure higher than atmospheric pressure to open an airway.

The CPAP device described in Patent Document 1 includes a first unit having a built-in blower and a second unit having a built-in humidifier. The first unit is attached to the second unit and can be used together with the second unit. In a state where the first unit is attached to the second unit, an air channel demarcated inside the first unit and an air channel demarcated inside the second unit communicate with each other. Also, in the state where the first unit is attached to the second unit, the first unit and the second unit are electrically connected via terminals of both the units and are capable of outputting and inputting signals and power to and from each other.

Patent Document 1: Japanese Unexamined Patent Application Publication (Translation of PCT Application) No. 2012-517850

BRIEF SUMMARY

In using the first unit together with the second unit in the CPAP device described in Patent Document 1, it is necessary to attach the first unit to the second unit such that the channel of the first unit is correctly aligned with the channel of the second unit and such that a terminal of the first unit is correctly aligned with a terminal of the second unit. However, depending on a positional relationship between the channel and the terminal of the first unit, correct alignment of both the channel and the terminal with the second unit may be difficult, and the attachment may take time.

In order to solve the above-described problem, an aspect of the present disclosure is a CPAP device for sending, into an airway of a user, air introduced into the device. The CPAP device includes: a first unit which has a built-in blower; and a second unit which has at least either one of a downstream-side channel through which air sent from the blower circulates and an upstream-side channel through which air sucked into the blower circulates and to which the first unit is to be removably attached. Either one of the first unit and the second unit has inside a cylindrical circulation portion through which air sent from the blower or sucked into the blower circulates. A base unit which is the other of the first unit and the second unit has a connection portion to which the circulation portion is to be connected. A first terminal with conductivity is provided at the circulation portion. An opening which causes an inside and an outside of the base unit to communicate and a second terminal with conductivity which contacts the first terminal while the first unit is attached to the second unit are provided at the connection portion.

With the above-described configuration, alignment of the circulation portion with the connection portion makes a positional deviation between the first terminal of the circulation portion and the second terminal of the connection portion less likely to occur. It is thus easier to attach the first unit to the second unit.

Alignment of the circulation portion with the connection portion in the CPAP device makes the first unit easier to attach to the second unit.

DETAILED DESCRIPTION

An embodiment of a CPAP device which sends, into an airway of a user, air introduced into the device will be described below with reference to the drawings. A schematic configuration of the CPAP device will be described first.

Figure 1:
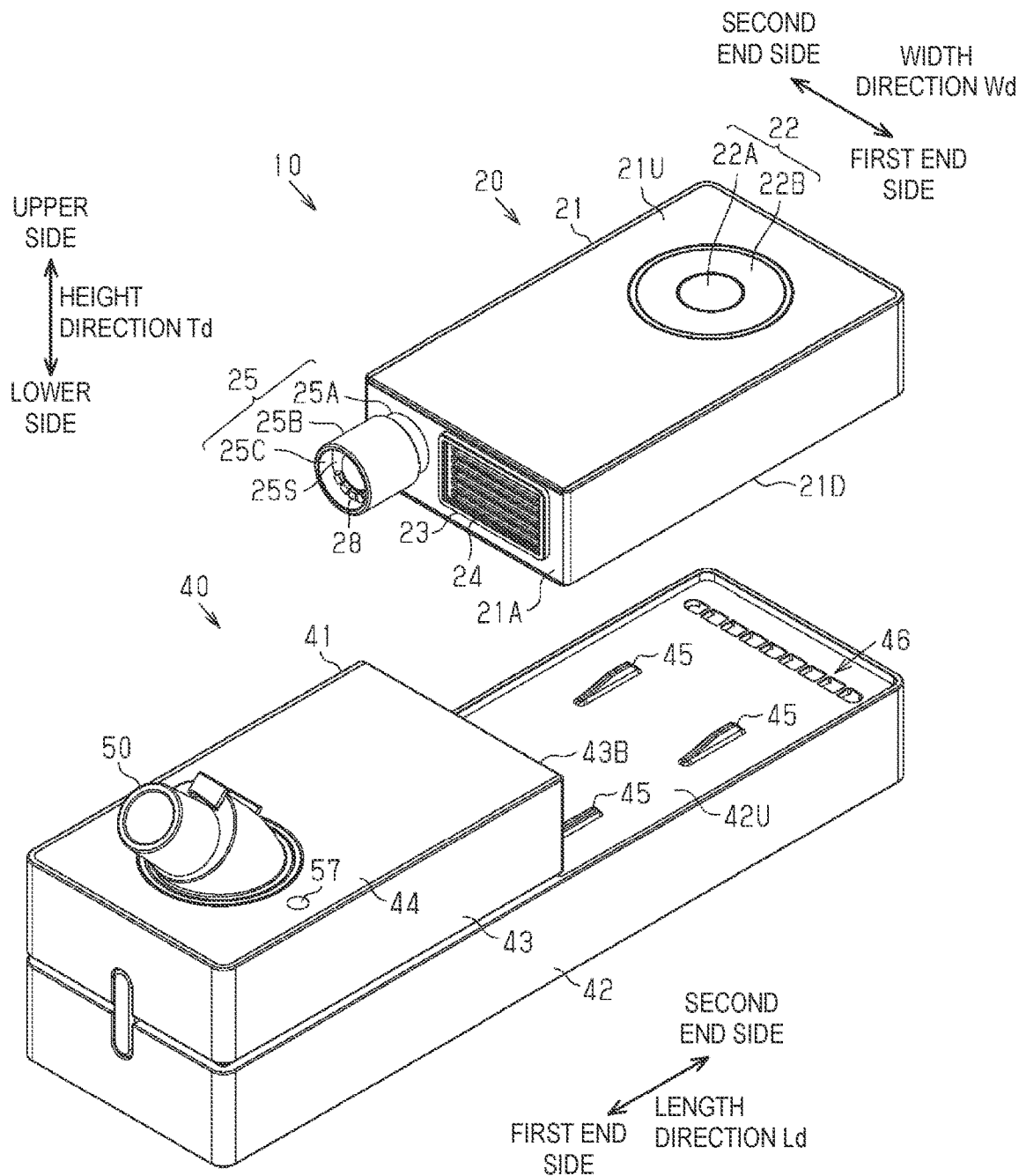
FIG. 1 is a perspective view showing a first unit and a second unit of a CPAP device.
Figure 3:
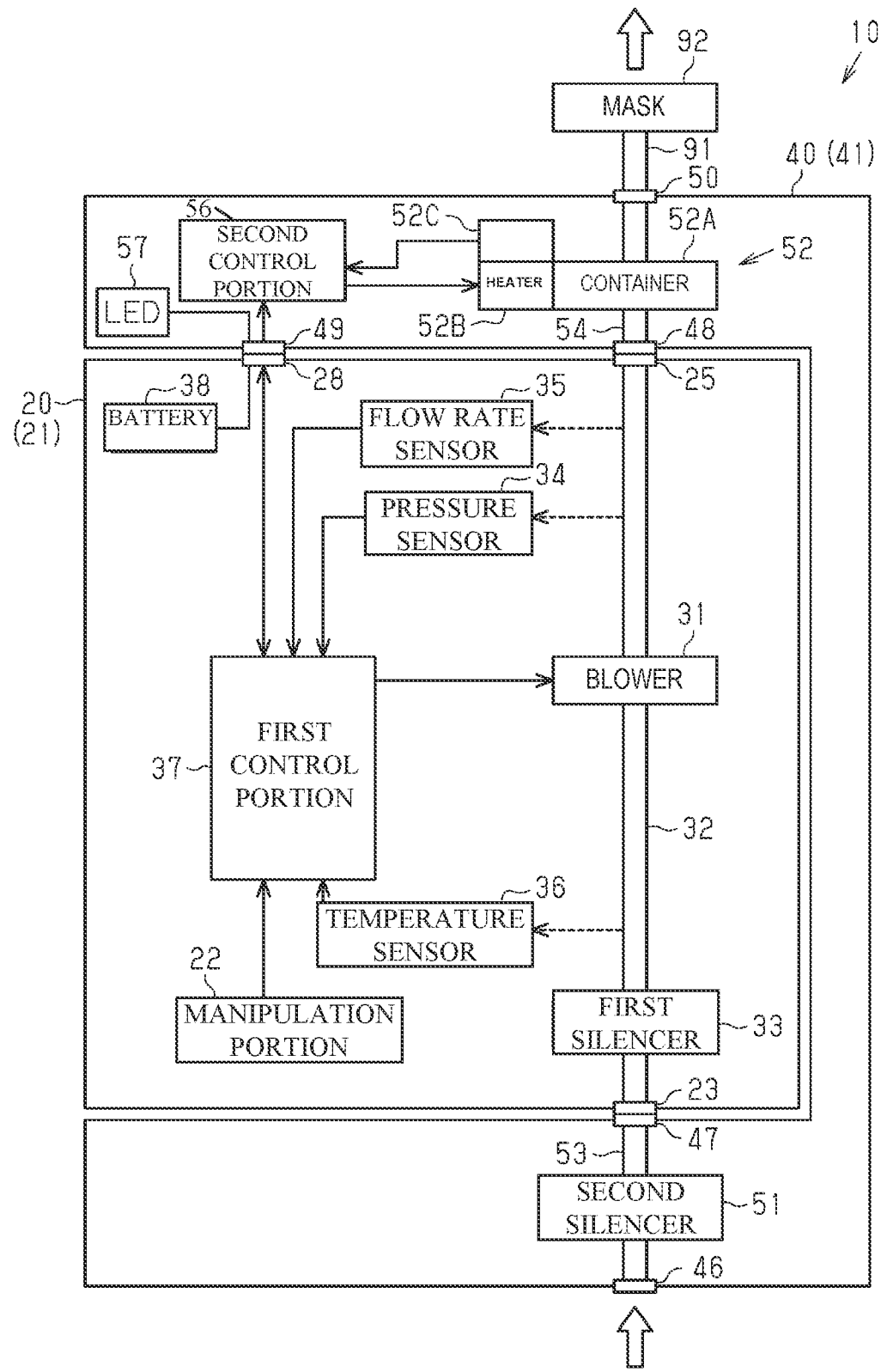
FIG. 3 is an explanatory diagram showing a schematic configuration of the CPAP device in the first usage state.

As shown in FIG. 1, a CPAP device 10 includes a body unit 20 as a first unit and a base unit 40 as a second unit. As shown in FIG. 3, the body unit 20 includes a blower 31 as a main component. The base unit 40 includes a second silencer 51 and a humidifier 52 as main components.

Figure 2:
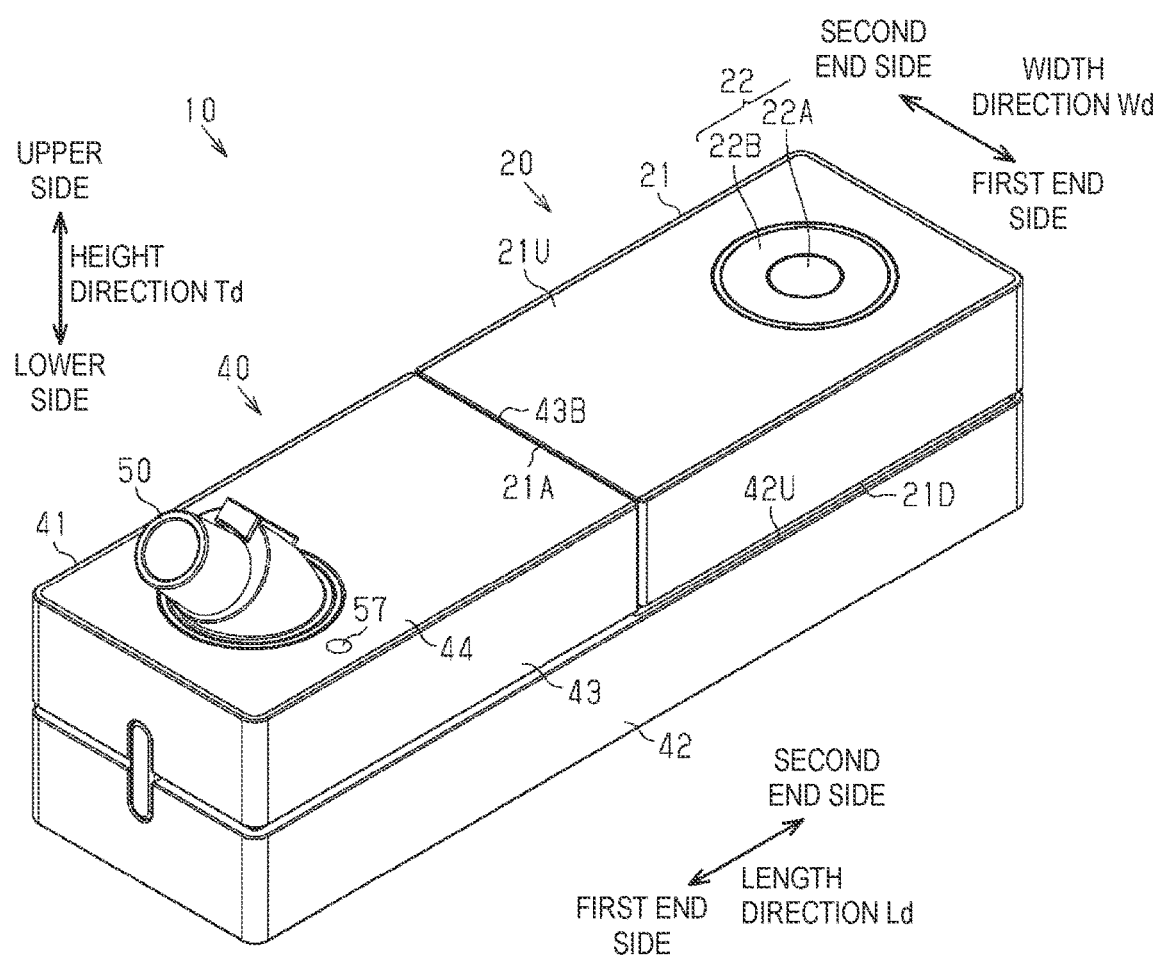
FIG. 2 is a perspective view showing the first unit and the second unit of the CPAP device in a first usage state.
Figure 4:
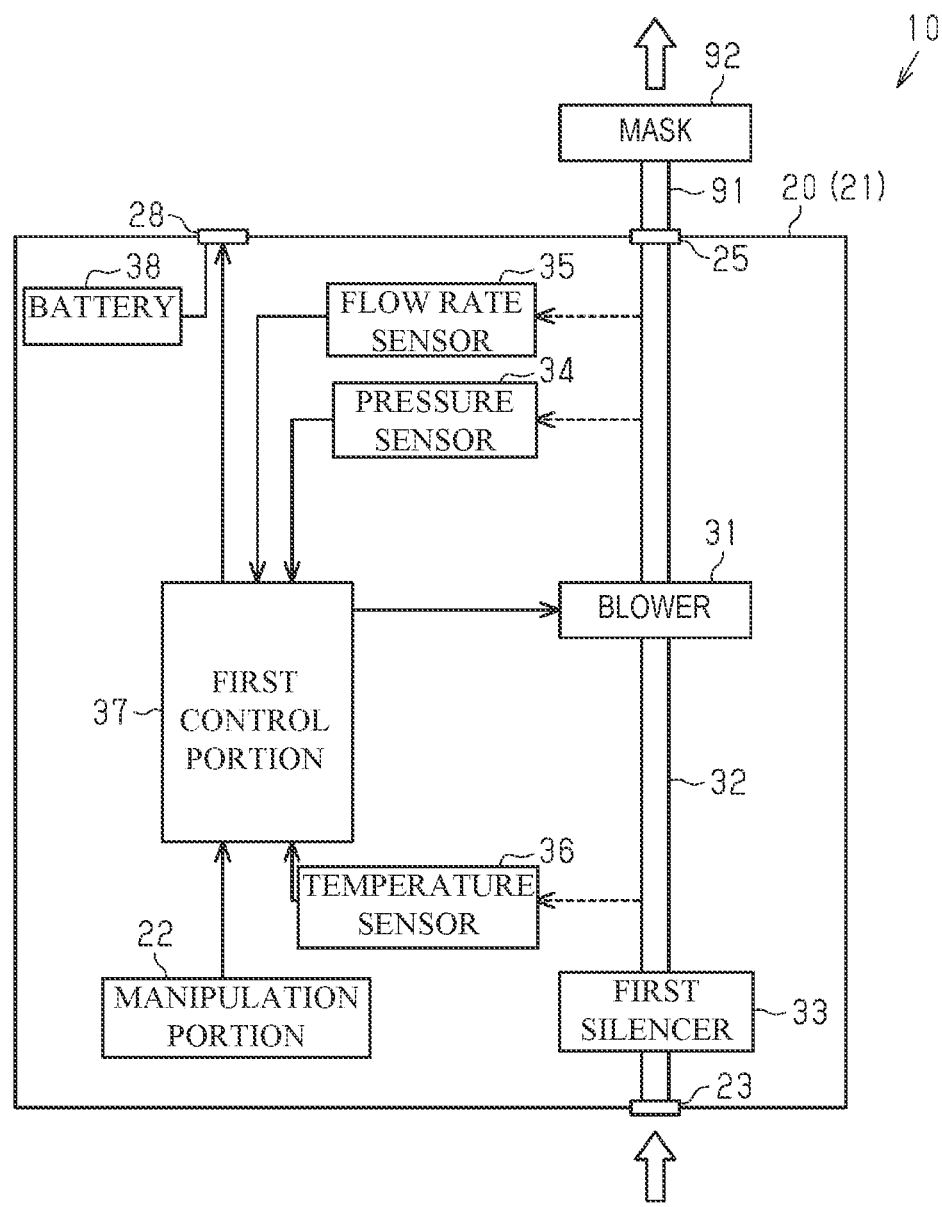
FIG. 4 is an explanatory diagram showing a schematic configuration of the CPAP device in a second usage state.

As shown in FIGS. 1 and 2, the body unit 20 is removable from the base unit 40. In the present embodiment, the CPAP device 10 is configured to be available for use in a first usage state and in a second usage state. The first usage state refers to a state where the CPAP device 10 is used while the body unit 20 is attached to the base unit 40, and the second usage state refers to a state where the CPAP device 10 is used while the body unit 20 is not attached to the base unit 40. In other words, in the first usage state, the body unit 20 and the base unit 40 are used, as shown in FIG. 3. As shown in FIG. 4, in the second usage state, only the body unit 20 is used, and the base unit 40 is not used.

Next, a configuration of the body unit 20 will be described.

As shown in FIG. 1, the body unit 20 includes a first housing 21 in the shape of a flat rectangular parallelepiped. The blower 31 and the like are built into the first housing 21, as shown in FIG. 4. Note that, in referring to directions with respect to the first housing 21, a thickness direction of the first housing 21 will be referred to as a height direction Td in the following description, as shown in FIG. 1. A long-side direction of the first housing 21 will be referred to as a length direction Ld, and a short-side direction of the first housing 21 will be referred to as a width direction Wd.

As shown in FIG. 1, a manipulation portion 22 for manipulating the body unit 20 is provided at an upper-side surface 21U of the first housing 21. In this embodiment, the manipulation portion 22 is composed of a circular switch 22A and an annular switch 22B which is arranged so as to surround the switch 22A. The switches 22A and 22B are both push-button switches, and manipulation of the switches 22A and 22B allows turn-on and turn-off of the body unit 20, change of settings, and the like.

At a first end face 21A which is an end face on a first end side in the length direction Ld in the first housing 21, a first introduction port 23 for introducing air from outside the first housing 21 to inside the first housing 21 is open. The first introduction port 23 has a substantially quadrangular shape in plan view. A filter 24 which filters dust or the like contained in air introduced into the first housing 21 is mounted over the first introduction port 23.

As shown in FIG. 4, a main channel 32 through which air circulates is demarcated inside the first housing 21 of the body unit 20. In the body unit 20, an upstream end of the main channel 32 is connected to the first introduction port 23. The blower 31 that sends out air from the first introduction port 23 to a downstream side is mounted in the middle of the main channel 32. The blower 31 is, for example, a centrifugal fan. In the main channel 32, a first silencer 33 is mounted between the first introduction port 23 and the blower 31. The first silencer 33 attenuates a circulation sound of air circulating through the main channel 32 with driving of the blower 31.

A pressure sensor 34 which detects a pressure of air downstream of the blower 31 inside the main channel 32 is mounted inside the first housing 21. A flow rate sensor 35 which detects a flow rate of air downstream of the blower 31 inside the main channel 32 is also mounted inside the first housing 21. A temperature sensor 36 which detects a temperature of air circulating through the main channel 32 is further mounted inside the first housing 21. A first lead-out portion 25 for leading out air from inside the first housing 21 to outside the first housing 21 is connected to a downstream end of the main channel 32.

As shown in FIG. 1, the first lead-out portion 25 protrudes from the first end face 21A of the first housing 21. The first lead-out portion 25 is arranged side by side with the first introduction port 23 in the width direction Wd of the first housing 21. The first lead-out portion 25 as a whole has the shape of a circular cylinder and protrudes from the first end face 21A along the length direction Ld. An inner space of the first lead-out portion 25 communicates with the main channel 32 inside the first housing 21. That is, in this embodiment, the first lead-out portion 25 is a cylindrical circulation portion through which air sent from the blower 31 circulates.

The first lead-out portion 25 can be roughly divided into a small-diameter portion 25A, a large-diameter portion 25B, and a thin-wall portion 25C in order from the first end face 21A side. An inner diameter of the large-diameter portion 25B is identical to an inner diameter of the small-diameter portion 25A while an outer diameter of the large-diameter portion 25B is larger than an outer diameter of the small-diameter portion 25A. As a result, an outer peripheral surface of the small-diameter portion 25A is recessed inward in a radial direction from an outer peripheral surface of the large-diameter portion 25B. An outer diameter of the thin-wall portion 25C is identical to the outer diameter of the large-diameter portion 25B while an inner diameter of the thin-wall portion 25C is larger than the inner diameter of the large-diameter portion 25B. As a result, a stepped portion 25S is formed at a boundary portion between an inner peripheral surface of the thin-wall portion 25C and an inner peripheral surface of the large-diameter portion 25B.

Figure 5:
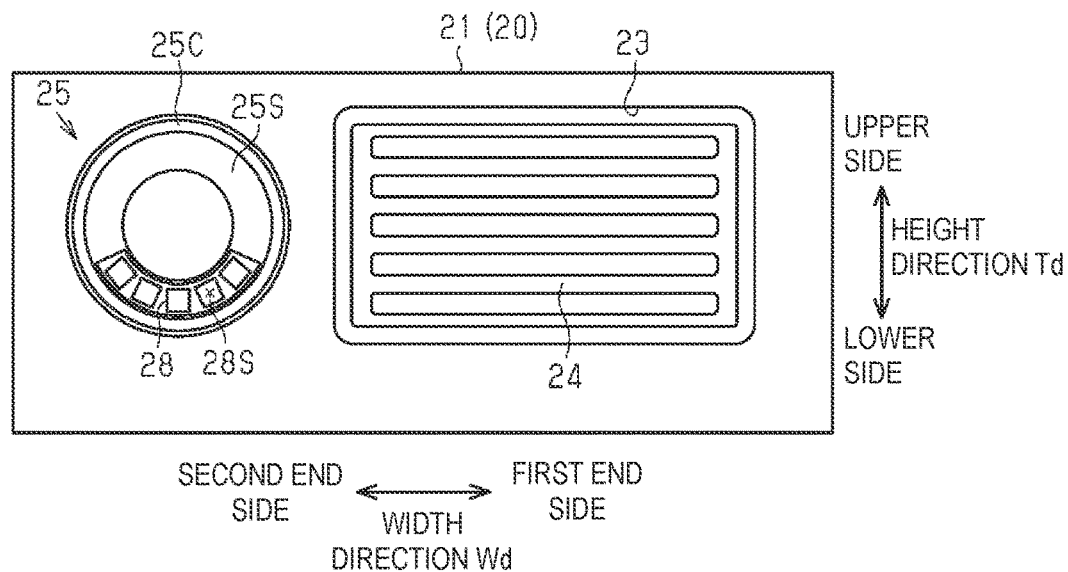
FIG. 5 is a plan view of a first end face of the first unit.

As shown in FIG. 5, five body-side terminals 28 are juxtaposed to one another as first terminals on the stepped portion 25S of the first lead-out portion 25. The body-side terminals 28 are arranged together on a lower side in the height direction Td on the stepped portion 25S. The body-side terminals 28 are lined up at regular intervals in a circumferential direction around a central axis of the first lead-out portion 25. Note that only one of the five body-side terminals 28 is denoted by a reference character in FIG. 5. In the present embodiment, the central axis of the first lead-out portion 25 passes through a center of an outer peripheral circle of the thin-wall portion 25C and a center of an inner peripheral circle of the thin-wall portion 25C. For this reason, the central axis of the first lead-out portion 25 is orthogonal to an aperture plane of the thin-wall portion 25C.

Figure 6:
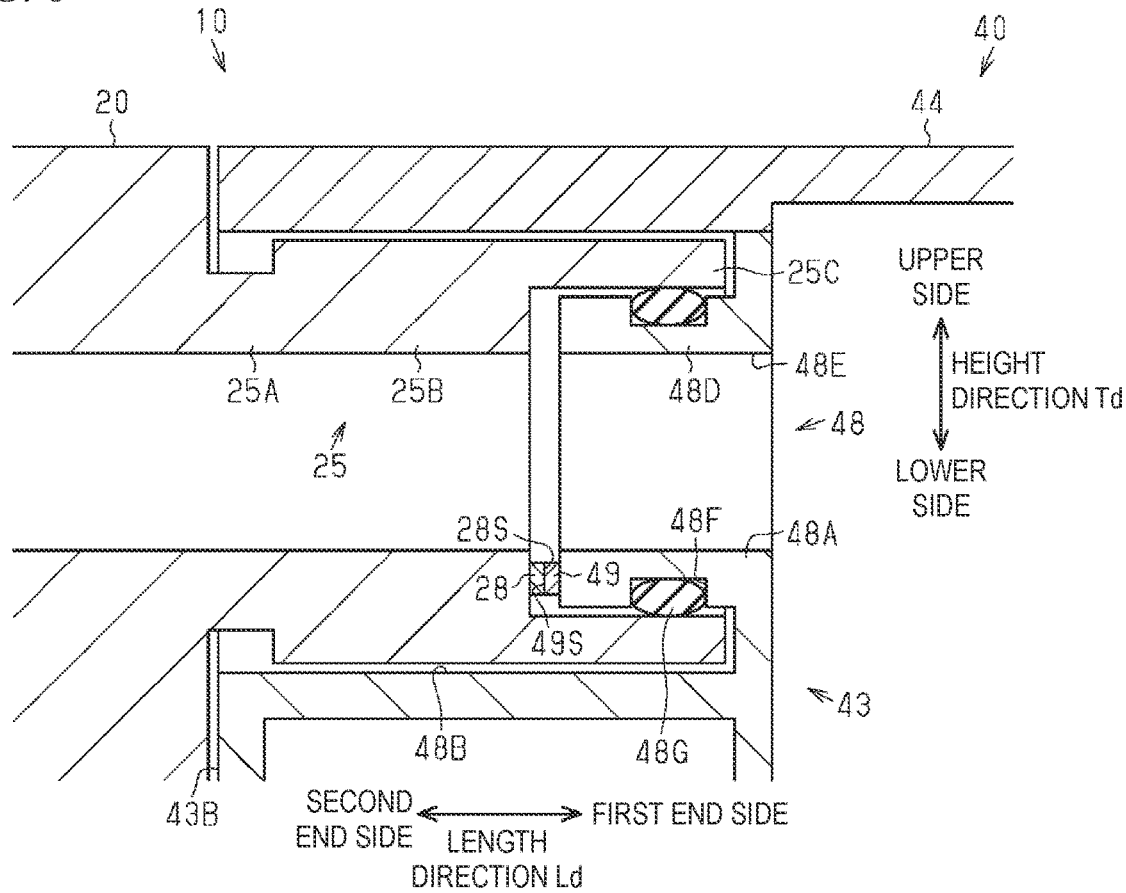
FIG. 6 is a partial sectional view showing a portion where the first unit and the second unit are connected.

As shown in FIG. 6, each body-side terminal 28 has a first contact surface 28S which is orthogonal to the central axis of the first lead-out portion 25. As shown in FIG. 5, the first contact surface 28S of the body-side terminal 28 is exposed when viewed from the first end side in the length direction Ld. In this embodiment, one of the five body-side terminals 28 is a power feeding terminal for feeding power from the body unit 20 side to the base unit 40 side. The other four of the five body-side terminals 28 are control terminals for exchanging control signals.

Next, an electrical configuration in the body unit 20 of the CPAP device 10 will be described.

As shown in FIG. 4, the body unit 20 includes a first control portion 37 for controlling operation of the blower 31. Note that the first control portion 37 is electrically connected to the control body-side terminals 28 by wiring (not shown).

The first control portion 37 can be constructed as a circuit (circuitry) including 1) one or more processors which execute various types of processes in accordance with a computer program (software), 2) one or more dedicated hardware circuits, such as an application-specific integrated circuit (ASIC), which execute at least one(s) of various processes, or 3) a combination thereof. A processor includes a CPU and memories, such as a RAM and a ROM, and the memories store program code or instructions configured to cause the CPU to execute processing. The memories, that is, computer-readable media include all available media accessible by a general-purpose or dedicated computer.

Inside the first housing 21 of the body unit 20, a battery 38 for feeding power to the blower 31, the pressure sensor 34, the flow rate sensor 35, the temperature sensor 36, and the first control portion 37 is provided. The battery 38 is a repeatedly rechargeable secondary battery and is charged when a charging cable (not shown) is connected to the body unit 20. Also, the battery 38 is electrically connected to the power feeding body-side terminal 28 of the body-side terminals 28.

A signal indicating a manipulation from the manipulation portion 22 is input to the first control portion 37. A pressure value detected by the pressure sensor 34 is input to the first control portion 37. A flow rate value detected by the flow rate sensor 35 is input to the first control portion 37. A temperature value detected by the temperature sensor 36 is input to the first control portion 37. The first control portion 37 is configured to increase or decrease the number of revolutions of the blower 31 by control, such as feedback control or feedforward control, on the basis of the input values to control an air delivery amount or the like. For example, the first control portion 37 assesses an exhaled breath state of a user on the basis of detected values from the pressure sensor 34 and the flow rate sensor 35 and controls a pressure value of air to be supplied to the user in synchronism with the exhaled breath state. The first control portion 37 also controls power feeding from the battery 38 to the power feeding body-side terminal 28.

Subsequently, a structure of the base unit 40 will be described.

Figure 7:
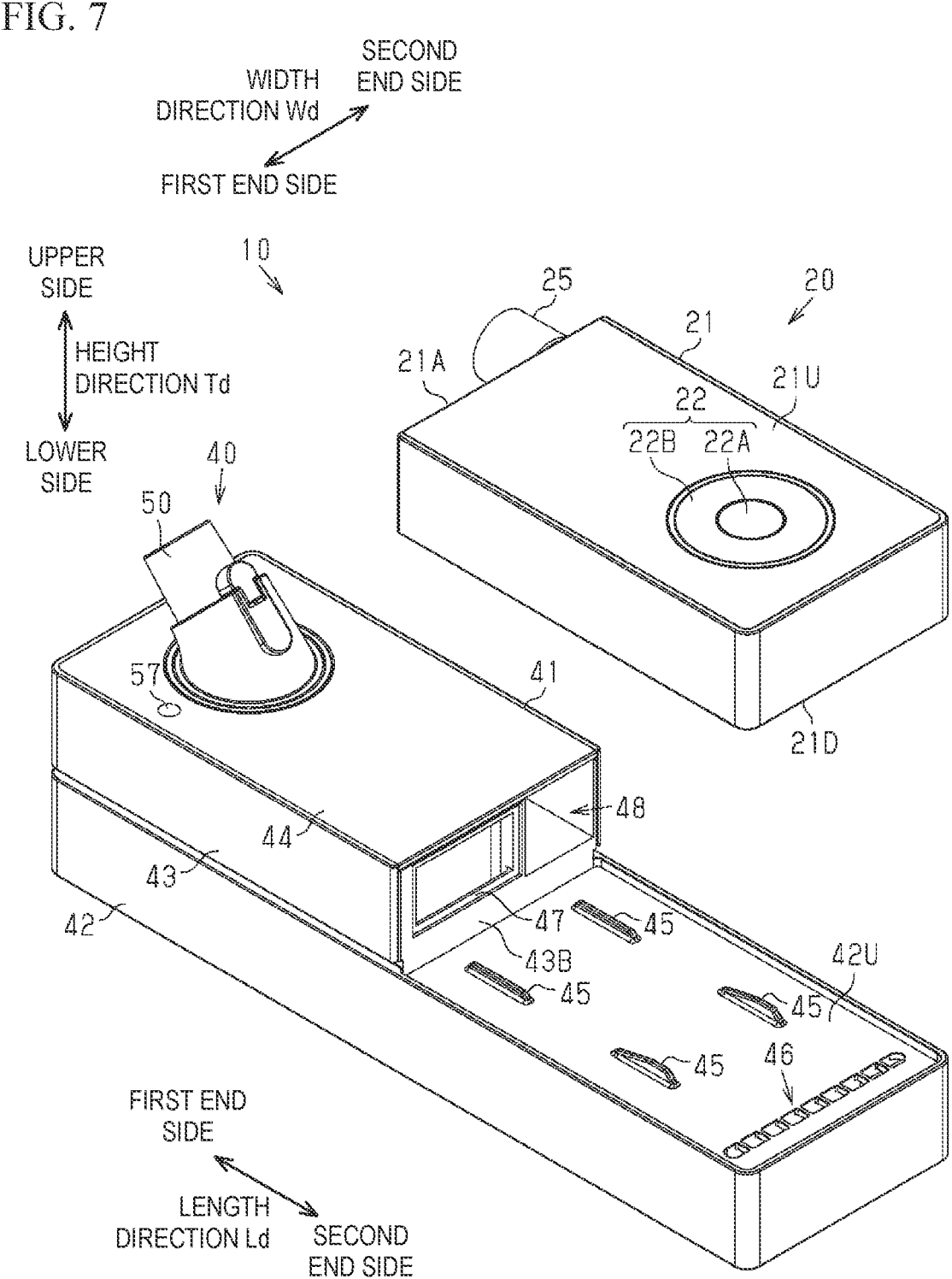
FIG. 7 is a perspective view of the CPAP device as viewed from a different angle from FIG. 1.

As shown in FIG. 7, the base unit 40 includes a second housing 41 in an L-shape in side view. The second housing 41 is roughly divided into a base housing 42 in the shape of a flat rectangular parallelepiped and a protruding housing 43 in the shape of a flat rectangular parallelepiped which is located on an upper side portion of the base housing 42.

A dimension in a longitudinal direction in the base housing 42 is larger than a dimension in the length direction Ld in the first housing 21. A dimension in a lateral direction in the base housing 42 is identical to a dimension in the width direction Wd in the first housing 21. Note that the following description assumes that the longitudinal direction of the base housing 42 of the second housing 41 is along the length direction Ld of the first housing 21 and that the lateral direction of the base housing 42 is along the width direction Wd of the first housing 21.

The protruding housing 43 protrudes from an upper surface on a first end side in a length direction Ld in the base housing 42. An end on the first end side in the length direction Ld of the protruding housing 43 coincides with an end on the first end side in the length direction Ld in the base housing 42. A dimension in a height direction Td in the protruding housing 43 is substantially identical to a dimension in the height direction Td in the first housing 21. A dimension in a width direction Wd in the protruding housing 43 is substantially identical to the dimension in the width direction Wd in the first housing 21. A dimension in the length direction Ld in the protruding housing 43 has a value obtained by subtracting the dimension in the length direction Ld in the first housing 21 from the dimension in the longitudinal direction in the base housing 42.

The base housing 42 and the protruding housing 43 each have the shape of a box having a hollow space inside. An inner space of the base housing 42 is continuous with an inner space of the protruding housing 43. A wall portion on the opposite side of the protruding housing 43 from the base housing 42, that is, an upper wall portion is constructed as an openable and closable lid 44. The lid 44 is configured to pivot around a side on the first end side in the length direction Ld as a rotation center. In a state where the lid 44 of the protruding housing 43 is pivoted and opened, the inner space of the protruding housing 43 and a part of the inner space of the base housing 42 are exposed.

A projection 45 which protrudes toward an upper side in the height direction Td of the base housing 42 is provided on an upper-side surface 42U of the base housing 42. In this embodiment, two projections 45 per row are provided along the length direction Ld of the base housing 42. Two rows of projections 45 are provided in the width direction Wd of the base housing 42. That is, a total of four projections 45 are provided.

At the upper-side surface 42U of the base housing 42, a second introduction port 46 for introducing air from outside the base housing 42 to inside the base housing 42 is open. In the present embodiment, a plurality of second introduction ports 46 are provided. The plurality of second introduction ports 46 are lined up so as to span the substantially entire gamut in the width direction Wd in the base housing 42. The second introduction ports 46 are arranged near an edge on a second end side in the length direction Ld of the upper-side surface 42U of the base housing 42. Note that, although details will be described later, the upper-side surface 42U of the base housing 42 functions as a surface on which the body unit 20 is to be placed.

As shown in FIG. 3, an upstream-side channel 53 through which air to be drawn into the blower 31 of the body unit 20 circulates is demarcated inside the second housing 41 of the base unit 40. In the base unit 40, an upstream end of the upstream-side channel 53 is connected to the second introduction ports 46.

The second silencer 51 is mounted in the middle of the upstream-side channel 53. The second silencer 51 attenuates a circulation sound of air circulating through the upstream-side channel 53. Note that the magnitude of a volume of the second silencer 51 is larger than a volume of the first silencer 33 of the body unit 20, and a sound attenuation effect is stronger than that of the first silencer 33 of the body unit 20.

A downstream end of the upstream-side channel 53 is connected to a second lead-out port 47 for leading out air from inside the second housing 41 to outside the second housing 41. As shown in FIG. 7, the second lead-out port 47 is open at a surface connected to the upper-side surface 42U of the base housing 42 of end faces on both sides in the length direction Ld of the protruding housing 43, that is, a second end face 43B which is a side surface on the second end side in the length direction Ld in the protruding housing 43. The second lead-out port 47 has a substantially quadrangular shape in plan view which is identical to the shape in plan view of the first introduction port 23 in the first housing 21.

As shown in FIG. 3, a downstream-side channel 54 through which air sent from the blower 31 of the body unit 20 circulates is demarcated inside the second housing 41 of the base unit 40. In the middle of the downstream-side channel 54, the humidifier 52 is mounted. The humidifier 52 includes a container 52A, a heater 52B, and a heater temperature sensor 52C. The container 52A is configured to be removable from the second housing 41 and is capable of storing water inside. Air introduced into the humidifier 52 passes through the container 52A and is led out of the humidifier 52, thereby humidifying the air. The heater 52B heats water in the container 52A. The heater temperature sensor 52C detects a temperature of the heater 52B. Note that, in this embodiment, opening of the lid 44 of the protruding housing 43 in the second housing 41 allows removal of the container 52A of the humidifier 52.

As shown in FIG. 7, a third lead-out portion 50 in the shape of a circular cylinder for leading out air from inside the second housing 41 to outside the second housing 41 protrudes from the lid 44 of the second housing 41. A central axis of the third lead-out portion 50 is inclined with respect to the height direction Td in the protruding housing 43. An inner space of the third lead-out portion 50 communicates with the inner space of the protruding housing 43.

A third introduction portion 48 is provided as a connection portion to which the first lead-out portion 25 in the body unit 20 is to be connected at the protruding housing 43 in the base unit 40. Specifically, as shown in FIG. 6, a recessed portion 48B of the third introduction portion 48 is recessed from the second end face 43B of the protruding housing 43 toward the first end side in the length direction Ld. The recessed portion 48B is open in a quadrangular shape as viewed from the length direction Ld. The dimension in the length direction Ld of the recessed portion 48B is substantially the same as a protrusion length of the first lead-out portion 25.

As shown in FIG. 7, the recessed portion 48B is arranged side by side with the second lead-out port 47 in the width direction Wd of the second housing 41. An upper-side portion of the recessed portion 48B is covered with the lid 44. That is, in a state where the lid 44 is open, the upper-side portion of the recessed portion 48B is open.

As shown in FIG. 6, a wall portion on the first end side in the length direction Ld of the recessed portion 48B is an inner wall 48A which demarcates a storage space of the humidifier 52. The inner wall 48A is parallel to the second end face 43B and stands side by side with the second end face 43B in the length direction Ld of the second housing 41. A through-hole 48E which has an identical dimension to an inner diameter of the first lead-out portion 25 extends through the inner wall 48A. The through-hole 48E is an opening which causes an inside and an outside of the base unit 40 to communicate, and communication with an inside of the container 52A of the humidifier 52 is achieved through the through-hole 48E. Note that the humidifier 52 is not shown in FIG. 6. A cylindrical connecting projection portion 48D protrudes from an opening edge of the through-hole 48E toward the second end side in the length direction Ld. The connecting projection portion 48D and the recessed portion 48B constitute the third introduction portion 48. An outer diameter of the connecting projection portion 48D is substantially the same as the inner diameter of the thin-wall portion 25C in the first lead-out portion 25. At an outer peripheral surface of the connecting projection portion 48D, a groove portion 48F is formed to span the gamut in a circumferential direction. A ring-shaped sealing member 48G is fit in the groove portion 48F.

Figure 8:
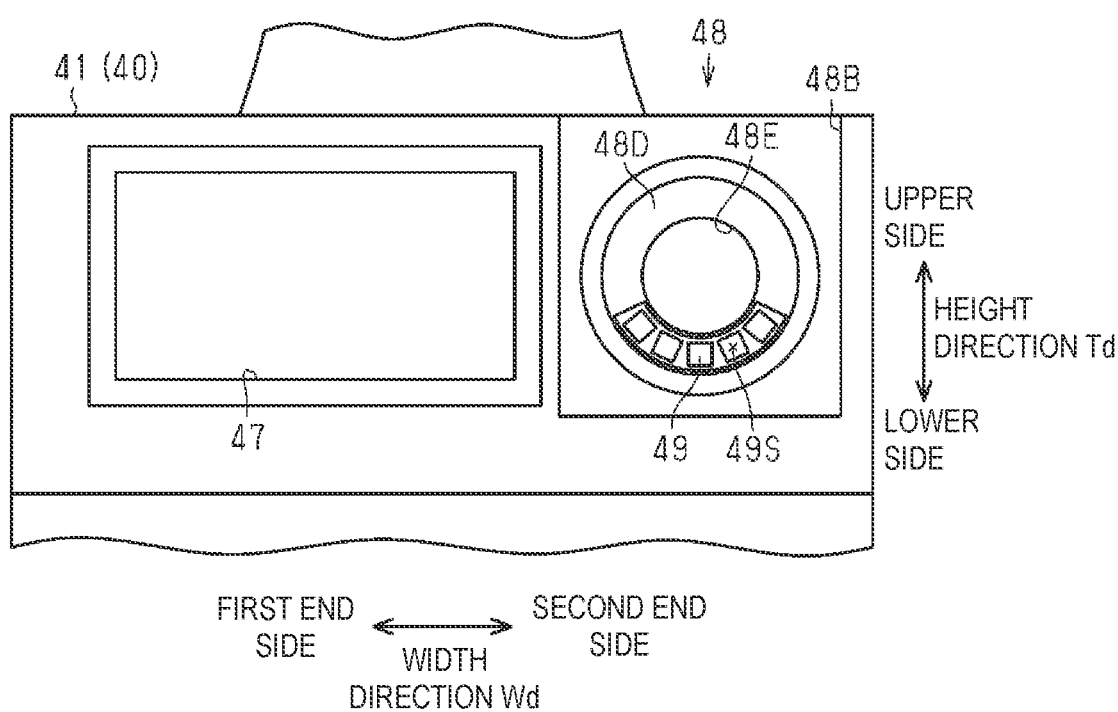
FIG. 8 is a plan view of a second end face of the second unit.

As shown in FIG. 8, five base-side terminals 49 are juxtaposed to one another as second terminals on a protruding distal end face of the connecting projection portion 48D. The base-side terminals 49 are arranged together on a lower side in the height direction Td on the protruding distal end face of the connecting projection portion 48D. The base-side terminals 49 are lined up at regular intervals in a circumferential direction around a central axis of the connecting projection portion 48D. An interval between the base-side terminals 49 is identical to an interval between the body-side terminals 28 in the body unit 20.

As shown in FIG. 6, each base-side terminal 49 has a second contact surface 49S which is orthogonal to the central axis of the connecting projection portion 48D, that is, a central axis of the through-hole 48E. As shown in FIG. 8, the second contact surface 49S of the base-side terminal 49 is exposed when viewed from the second end side in the length direction Ld. As shown in FIG. 6, the second contact surface 49S of the base-side terminal 49 is provided so as to be parallel to the first contact surface 28S of the body-side terminal 28 when both the body unit 20 and the base unit 40 are arranged such that the central axis of the first lead-out portion 25 of the body unit 20 coincides with the central axis of the through-hole 48E. That is, when the first lead-out portion 25 of the body unit 20 is housed in the third introduction portion 48 of the base unit 40, the second contact surface 49S of the base-side terminal 49 faces the first contact surface 28S of the body-side terminal 28. In this embodiment, one of the five base-side terminals 49 is a power feeding terminal corresponding to the power feeding body-side terminal 28. The other four of the five base-side terminals 49 are control terminals corresponding to the control body-side terminals 28.

An electrical configuration in the base unit 40 of the CPAP device 10 will be described.

As shown in FIG. 3, the base unit 40 includes a second control portion 56 which controls operation of the heater 52B. The second control portion 56 can be constructed as a circuit (circuitry) including 1) one or more processors which execute various types of processes in accordance with a computer program (software), 2) one or more dedicated hardware circuits, such as an application-specific integrated circuit (ASIC), which execute at least one(s) of various processes, or 3) a combination thereof. A processor includes a CPU and memories, such as a RAM and a ROM, and the memories store program code or instructions configured to cause the CPU to execute processing. The memories, that is, computer-readable media include all available media accessible by a general-purpose or dedicated computer.

Power is fed from the battery 38 of the body unit 20 to the second control portion 56 via the power feeding body-side terminal 28 of the body unit 20 and the power feeding base-side terminal 49. A signal indicating an air temperature value detected by the temperature sensor 36 is input from the first control portion 37 to the second control portion 56 via the control body-side terminal 28 of the body unit 20 and the control base-side terminal 49.

An LED lamp 57 is provided on the base unit 40 as a notification portion for notifying that the body unit 20 is attached to the base unit 40. The LED lamp 57 is electrically connected to the power feeding base-side terminal 49 via an electric circuit (not shown). As shown in FIG. 2, a light emission portion of the LED lamp 57 is exposed from the lid 44 such that visual recognition from the outside is possible even in a state with the lid 44 closed.

The second control portion 56 sets a target heater temperature for heating the water in the container 52A on the basis of an input air temperature value. For example, the second control portion 56 sets the target heater temperature by a computation expression determined in advance. The second control portion 56 is configured to drive the heater 52B by control, such as feedback control or feedforward control, on the basis of a heater temperature detected by the heater temperature sensor 52C so as to set the heater temperature to the target heater temperature. The second control portion 56 adjusts a water temperature inside the container 52A by the heater 52B. When the heater temperature reaches the target heater temperature, the second control portion 56 controls the heater 52B so as to keep the heater temperature at the target heater temperature.

Subsequently, action of the CPAP device 10 in the first usage state will be described.

Figure 9:
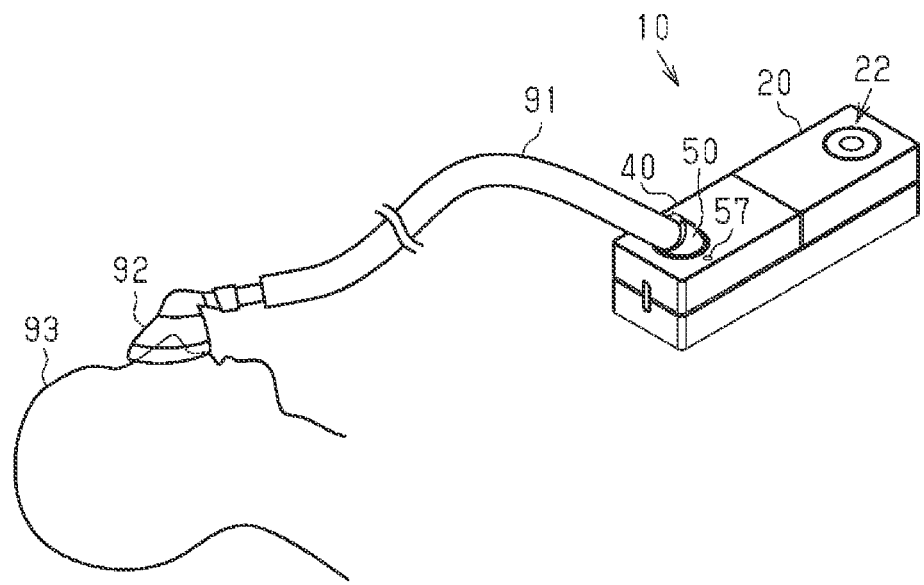
FIG. 9 is a schematic view showing the first usage state of the CPAP device.

As shown in FIG. 9, in the first usage state, the body unit 20 is attached to the base unit 40. Specifically, as shown in FIG. 2, the body unit 20 is placed on the base unit 40 such that a lower-side surface 21D in the first housing 21 faces the upper-side surface 42U of the base housing 42 in the second housing 41. The first end face 21A in the first housing 21 faces and is in contact with the second end face 43B of the protruding housing 43 in the second housing 41. Thus, in the first usage state, the CPAP device 10 as a whole has the shape of an elongated rectangular parallelepiped.

As shown in FIG. 3, in the first usage state, the first introduction port 23 of the first housing 21 is connected to the second lead-out port 47 of the second housing 41, and the upstream end of the main channel 32 of the body unit 20 is connected to the downstream end of the upstream-side channel 53 of the base unit 40 via the first introduction port 23 and the second lead-out port 47. The first lead-out portion 25 of the first housing 21 is inserted into the third introduction portion 48 of the second housing 41, and the downstream end of the main channel 32 of the body unit 20 is connected to an upstream end of the downstream-side channel 54 of the base unit 40 via the first lead-out portion 25 and the third introduction portion 48. As shown in FIG. 6, the first contact surfaces 28S of the body-side terminals 28 of the first housing 21 are in surface contact with the second contact surfaces 49S of the base-side terminals 49 of the second housing 41.

As shown in FIG. 9, in the first usage state, a first end portion of an air tube 91 is connected to the third lead-out portion 50 of the base unit 40, and a second end portion of the air tube 91 is connected to a mask 92. The mask 92 is worn so as to, for example, cover a nose or a mouth of a user 93.

In the first usage state of the CPAP device 10, when the manipulation portion 22 of the body unit 20 is manipulated and the body unit 20 is turned on, the blower 31 is driven. With the projections 45 provided on the upper-side surface 42U of the base housing 42 of the base unit 40, there is a gap between the lower-side surface 21D of the first housing 21 and the second introduction ports 46. For this reason, air is sucked from the gap into the CPAP device 10 through the second introduction ports 46. The air sucked into the CPAP device 10 passes through the upstream-side channel 53 of the second housing 41, the main channel 32 of the first housing 21, and the downstream-side channel 54 of the second housing 41 and is discharged to the outside through the third lead-out portion 50 of the second housing 41. With this discharge, the air is sent into an airway of the user 93 via the air tube 91 and the mask 92.

As shown in FIG. 3, in the first usage state of the CPAP device 10, the body-side terminals 28 of the body unit 20 and the base-side terminals 49 of the base unit 40 contact each other to be electrically continuous. For this reason, power is supplied from the battery 38 of the body unit 20 to the LED lamp 57 via the body-side terminal 28 and the base-side terminal 49 to light up the LED lamp 57.

Next, the CPAP device in the second usage state will be described.

Figure 10:
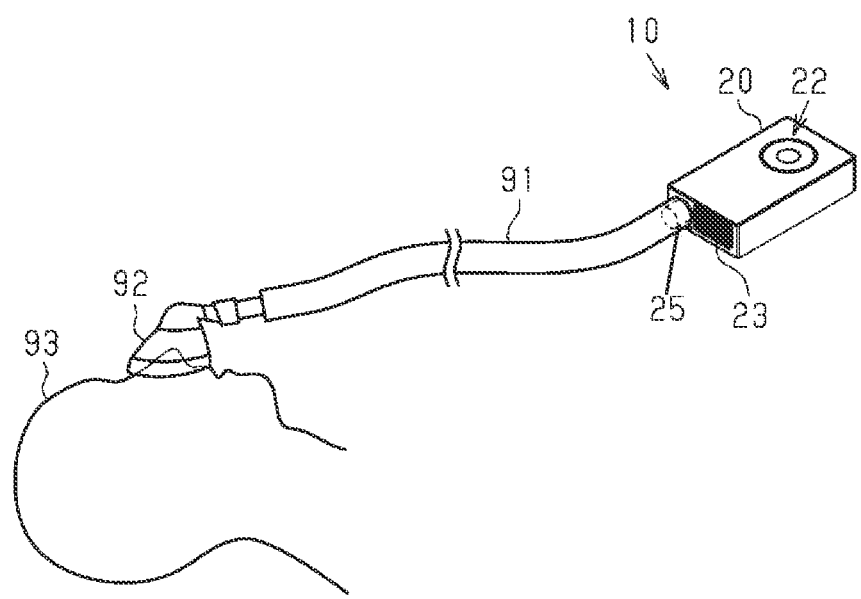
FIG. 10 is a schematic view showing the second usage state of the CPAP device.

As shown in FIG. 10, in the second usage state, the body unit 20 is not attached to the base unit 40 in the CPAP device 10, that is, only the body unit 20 is used. In this case, the first end portion of the air tube 91 is connected to the first lead-out portion 25 of the body unit 20, and the second end portion of the air tube 91 is connected to the mask 92. The mask 92 is worn so as to, for example, cover the nose or the mouth of the user 93. Note that, since the body unit 20 is not attached to the base unit 40 in the second usage state, no power is supplied to the LED lamp 57 of the base unit 40. Thus, the LED lamp 57 of the base unit 40 does not light up and remains off.

Effects of the above-described embodiment will be described.

(1) Assume attachment of the body unit 20 to the base unit 40 in the CPAP device 10. In this case, for example, the connecting projection portion 48D of the base unit 40 is inserted into the first lead-out portion 25 of the body unit 20 while both the units are aligned such that the central axis of the first lead-out portion 25 of the body unit 20 coincides with the central axis of the connecting projection portion 48D of the base unit 40, as shown in FIG. 6. Even if the body unit 20 is attached to the base unit 40, as described above, the first lead-out portion 25 of the body unit 20 can rotate in the circumferential direction around the central axis relative to the connecting projection portion 48D of the base unit 40. If the body-side terminals 28 of the body unit 20 are arranged at positions distant in a radial direction from the central axis of the first lead-out portion 25, the body-side terminals 28 deviate positionally from the base-side terminals 49 of the base unit 40 with only slight relative rotation of the body unit 20. This prevents contact between both the terminals.

In the embodiment, the body-side terminals 28 are provided on the first lead-out portion 25, and a distance from the body-side terminals 28 to the central axis of the first lead-out portion 25 is small. For this reason, even if the body unit 20 rotates relatively to a certain extent, a positional deviation which brings the body-side terminals 28 out of contact with the base-side terminals 49 is unlikely to occur. Thus, the body unit 20 can be easily attached to the base unit 40 such that the body-side terminals 28 correctly contact the base-side terminals 49.

(2) In the embodiment, the body-side terminals 28 are arranged on, of the first lead-out portion 25 of the body unit 20, the stepped portion 25S that is an inner-side portion in the radial direction of the first lead-out portion 25. The arrangement of the body-side terminals 28 at positions as close as possible to the central axis of the first lead-out portion 25 makes it possible to more suitably suppress a positional deviation of the body-side terminals 28 from the base-side terminals 49.

(3) In the embodiment, when the body-side terminal 28 of the body unit 20 contacts the base-side terminal 49 of the base unit 40, the LED lamp 57 lights up. For this reason, electrically correct connection of the body unit 20 and the base unit 40 can be known by visually recognizing lighting-up of the LED lamp 57.

(4) In the embodiment, in a state where the central axis of the first lead-out portion 25 in the body unit 20 coincides with the central axis of the through-hole 48E in the base unit 40, the first contact surfaces 28S of the body-side terminals 28 are arranged parallel to the second contact surfaces 49S of the base-side terminals 49. In a state where the body unit 20 is attached to the base unit 40, the first contact surfaces 28S of the body-side terminals 28 are in surface contact with the second contact surfaces 49S of the base-side terminals 49. That is, in the embodiment, the LED lamp 57 does not light up unless the body unit 20 is pushed into the base unit 40 in the length direction Ld as far as the body unit 20 goes. For this reason, when the LED lamp 57 lights up, the first end face 21A of the body unit 20 is in contact with the second end face 43B of the base unit 40, and the channel inside the body unit 20 and the channels inside the base unit 40 are correctly connected. Thus, a situation where although the body unit 20 is attached to the base unit 40, and electrical connection between both the units is established, the channels are not correctly connected, and air leaks out is unlikely to occur.

(5) In the embodiment, the first introduction port 23 and the first lead-out portion 25 of the body unit 20 are connected to the second lead-out port 47 and the third introduction portion 48 of the base unit 40. That is, in the embodiment, it is suitable to perform alignment at one electrical connection point and two channel connection points, a total of three connection points and attach the body unit 20 to the base unit 40. A configuration related to arrangement of the body-side terminals 28 and the base-side terminals 49 as in the embodiment by a device with many points to be aligned can be adopted in that the adoption reduces the trouble of attaching the body unit 20 to the base unit 40.

The above-described embodiment can be changed in the following manner and carried out. The embodiment and the following modifications can be combined and carried out without necessarily technical contradiction.

As for the embodiment, the configuration of the body unit 20 is not limited to the example in the embodiment. For example, a humidifier may be provided inside the body unit 20.

As for the embodiment, the configuration of the base unit 40 is not limited to the example in the embodiment. For example, either one or both of the second silencer 51 and the humidifier 52 may be omitted from the base unit 40. A function of giving perfume or medicinal properties may be added to the humidifier 52 of the base unit 40. Note that, if the second silencer 51 of the base unit 40 is omitted, the upstream-side channel 53 and the like can be omitted from the base unit 40. If the humidifier 52 of the base unit 40 is omitted, the downstream-side channel 54 and the like can be omitted from the base unit 40. Anything may be adopted as the base unit 40 as long as at least either one of the downstream-side channel 54, through which air sent from the blower 31 circulates, and the upstream-side channel 53, through which air sucked into the blower 31 circulates, is demarcated, as described above.

Although the embodiment has a configuration in which the first lead-out portion 25 of the body unit 20 is to be inserted into the recessed portion 48B of the third introduction portion 48 of the base unit 40, the projection-recess relationship may be reversed. That is, a component corresponding to the third introduction portion 48 may be provided at the body unit 20, and a component corresponding to the first lead-out portion 25 may be provided at the base unit 40.

Components corresponding to the first lead-out portion 25 and the third introduction portion 48 according to the embodiment may be provided at a connection point between the upstream end of the main channel 32 of the body unit 20 and the downstream end of the upstream-side channel 53 of the base unit 40.

As for the embodiment, the shapes and dimensions of the first lead-out portion 25 and the third introduction portion 48 are not limited to the examples in the embodiment. The first lead-out portion 25 may have the shape of a rectangular cylinder, the recessed portion 48B of the third introduction portion 48 may be open in a circular shape as viewed from the length direction Ld, or the third introduction portion 48 may have a shape protruding from the second end face 43B. Alternatively, as for the shape of the first lead-out portion 25, a center of an outer peripheral circle need not coincide with a center of an inner peripheral circle. In this case, a first contact surface and a second contact surface only need to face each other when an axis orthogonal to the opening plane of the first lead-out portion 25 as the circulation portion is arranged parallel to an axis orthogonal to an opening plane of the third introduction portion 48 as the connection portion.

The shapes and the like of the body-side terminals 28 of the body unit 20 and the base-side terminals 49 of the base unit 40 are not particularly limited as long as electrical connection can be ensured when the body unit 20 is attached to the base unit 40.

Figure 11:
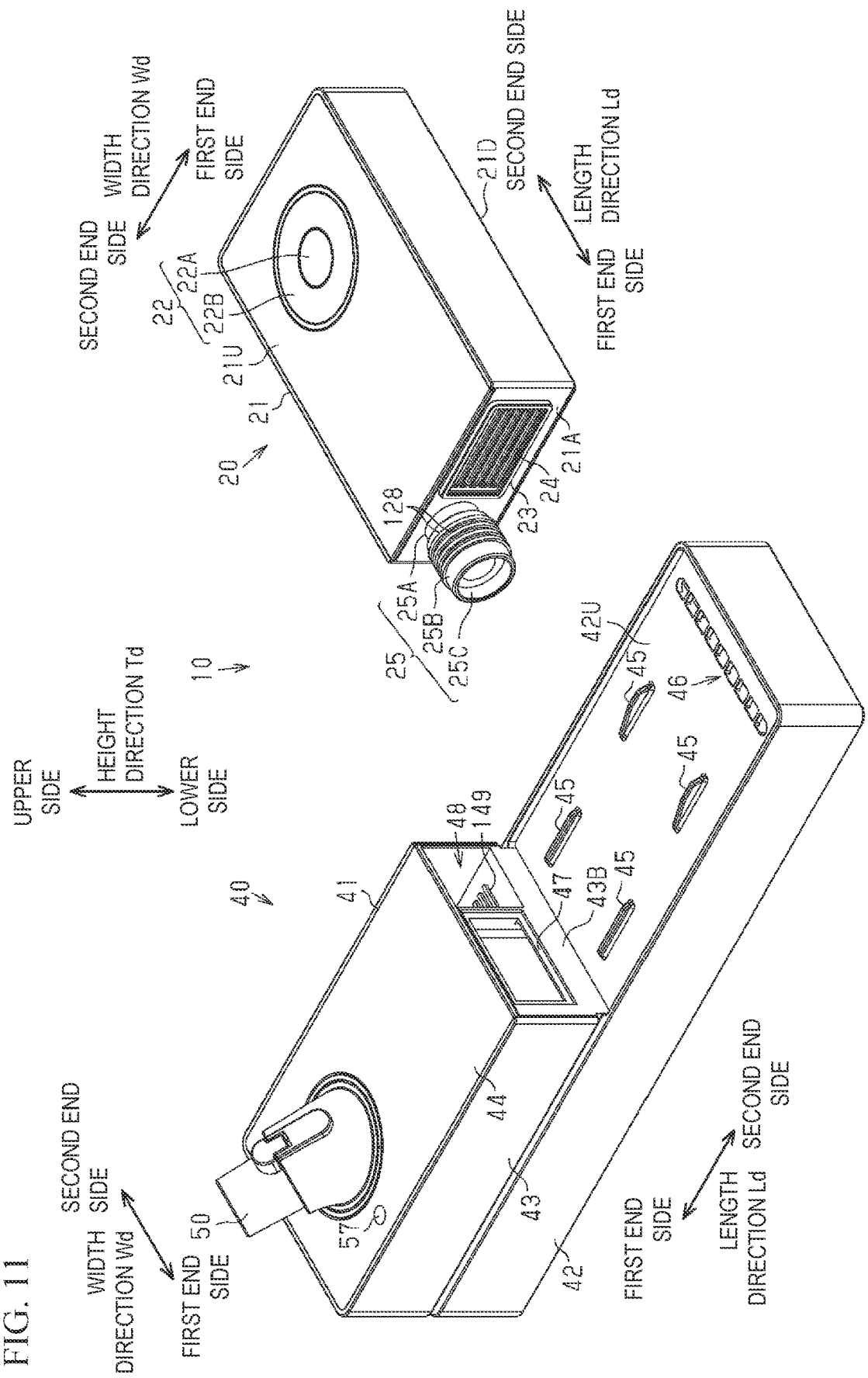
FIG. 11 is a perspective view showing a first unit and a second unit according to a modification.

Specifically, in an example shown in FIG. 11, four body-side terminals 128 are provided as first terminals on an outer peripheral surface of the large-diameter portion 25B of the first lead-out portion 25 in the body unit 20. The body-side terminals 128 extend annularly to span the entire gamut in a circumferential direction of the first lead-out portion 25. The body-side terminals 128 are exposed outward in a radial direction of the first lead-out portion 25. The body-side terminals 128 are provided at regular intervals in an axial direction of the first lead-out portion 25. Four base-side terminals 149 are provided as second terminals on an inner wall surface of the recessed portion 48B of the third introduction portion 48 in the base unit 40. The base-side terminals 149 are provided on a wall surface on a lower side in a height direction Td of the base unit 40. The base-side terminals 149 extend linearly along a width direction Wd of the base unit 40. The base-side terminals 149 are provided at regular intervals in a length direction Ld of the base unit 40. An interval in the length direction Ld between the base-side terminals 149 is equal to an interval between the body-side terminals 128 in the axial direction of the first lead-out portion 25.

Figure 12:
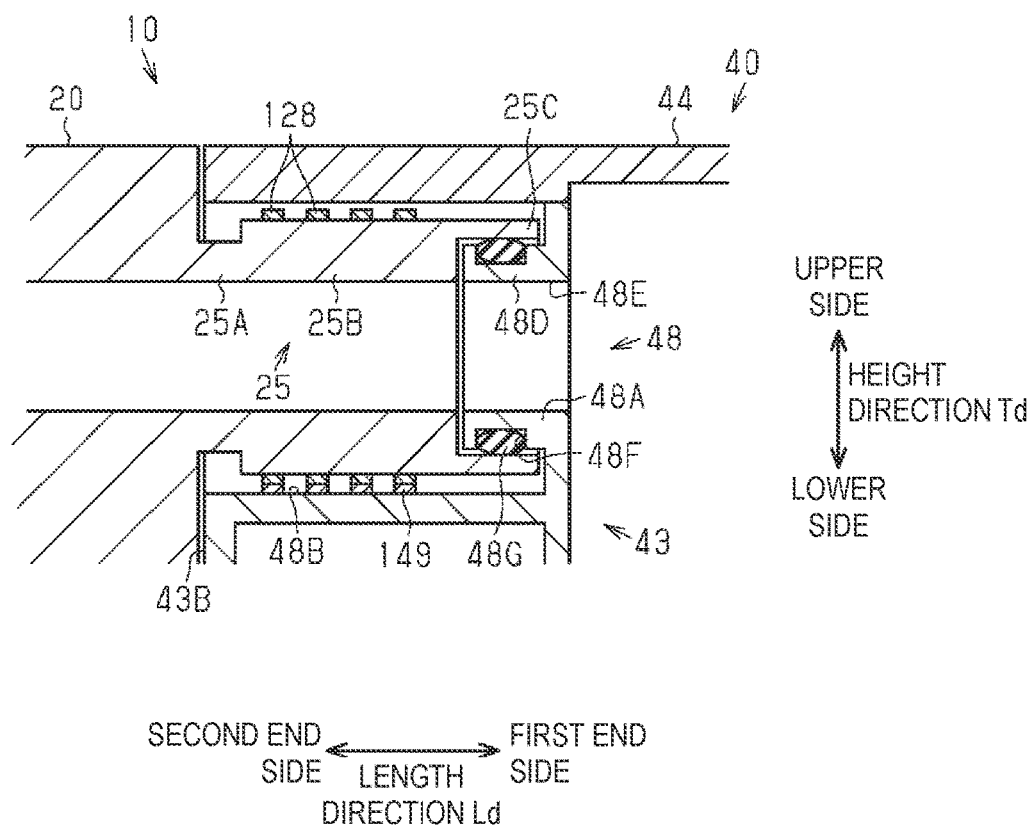
FIG. 12 is a partial sectional view showing a portion where the first unit and the second unit according to the modification are connected.

In the modification, when the body unit 20 is attached to the base unit 40, a portion on the lower side in the height direction Td of each body-side terminal 128 of the first lead-out portion 25 contacts the base-side terminal 149 of the third introduction portion 48, as shown in FIG. 12. Since the body-side terminals 128 of the first lead-out portion 25 extend annularly around a central axis of the first lead-out portion 25, even if the body unit 20 rotates around the central axis of the first lead-out portion 25 relative to the base unit 40, a contact relationship between both the terminals is maintained.

In the modification, the body-side terminals 128 that are exposed inward in the radial direction may be provided on an inner peripheral surface of the first lead-out portion 25 (for example, an inner peripheral surface of the thin-wall portion 25C). In this case, the base-side terminals 149 may be provided on an outer peripheral surface of the connecting projection portion 48D of the base unit 40.

In providing the body-side terminals 28 on the first lead-out portion 25 of the body unit 20, the body-side terminals 28 can also be arranged outside an outer peripheral surface of the first lead-out portion 25 in the radial direction. For example, a portion which protrudes outward from the outer peripheral surface of the first lead-out portion 25 in the radial direction is provided. A recessed female connector is provided on a second end side in a length direction Ld of the protruding portion, and the body-side terminal 28 is provided inside the connector. A protruding male connector is provided on a second end side in the length direction Ld inside the third introduction portion 48 of the base unit 40, and the base-side terminal 49 is provided inside the connector. If the male connector of the base unit 40 is inserted into the female connector of the body unit 20 when the body unit 20 is attached to the base unit 40, electrical continuity between the body-side terminal 28 and the base-side terminal 49 is ensured.

In the embodiment, the notification portion is not limited to the LED lamp 57. For example, the notification portion may be a buzzer which emits sound. Note that, if a buzzer is adopted as the notification portion, for example, sound may be emitted for a fixed period (for example, several seconds) after the body-side terminal 28 contacts the base-side terminal 49, and current starts flowing through the buzzer. Alternatively, the LED lamp 57 and another type of notification portion, such as a buzzer, may be used in combination.

In the embodiment, the LED lamp 57 may be provided at the body unit 20. In this case, the LED lamp 57 may be provided on a closed circuit which is formed when the body-side terminal 28 contacts the base-side terminal 49.

In the embodiment, the LED lamp 57 can be omitted. As described above, in the embodiment, the body-side terminals 28 are unlikely to deviate positionally from the base-side terminals 49 at the time of attaching the body unit 20 to the base unit 40, and electrical connection between both the units is ensured. Thus, there is no particular harm in omitting the LED lamp 57 for notification.

In the embodiment, a battery may also be provided in the base unit 40. If a battery is provided in the base unit 40, a configuration may be adopted in which power can be fed from the battery of the base unit 40 to the battery 38 of the body unit 20 via the base-side terminal 49 and the body-side terminal 28 when the body unit 20 is attached to the base unit 40.

REFERENCE SIGNS LIST

10 CPAP device
20 body unit
21 first housing
21A first end face
21D lower-side surface
21U upper-side surface
22 manipulation portion
22A switch
22B switch
23 first introduction port
24 filter
25 first lead-out portion
25A small-diameter portion
25B large-diameter portion
25C thin-wall portion
25S stepped portion
28 body-side terminal
28S first contact surface
31 blower
32 main channel
33 first silencer
34 pressure sensor
35 flow rate sensor
36 temperature sensor
37 first control portion
38 battery
40 base unit
41 second housing
42 base housing
42U upper-side surface
43 protruding housing
43B second end face
44 lid
45 projection
46 second introduction port
47 second lead-out port
48 third introduction portion
48A inner wall
48B recessed portion
48D connecting projection portion
48E through-hole
48F groove portion
48G sealing member
49 base-side terminal
49S second contact surface
50 third lead-out portion
51 second silencer
52 humidifier
52A container
52B heater
52C heater temperature sensor
53 upstream-side channel
54 downstream-side channel
56 second control portion
57 LED lamp
91 air tube
92 mask
93 user
128 body-side terminal
149 base-side terminal

The invention claimed is:

1. A CPAP device that is configured to send, into an airway of a user, air introduced into the device, the CPAP device comprising:
   a first unit which has a built-in blower; and
   a second unit which has at least either one of a downstream-side channel through which air sent from the blower circulates, and an upstream-side channel through which air sucked into the blower circulates and to which the first unit is removably attached, wherein
   the first unit has a cylindrical circulation portion through which air sent from the blower or sucked into the blower circulates,
   a base unit that is the second unit has a connection portion to which the cylindrical circulation portion is connected,
   the cylindrical circulation portion comprises a first terminal with conductivity, and
   the connection portion comprises an opening which communicates an inside and an outside of the base unit, and a second terminal with conductivity which contacts the first terminal while the first unit is attached to the second unit, wherein
   the second unit has the downstream-side channel, through which air sent from the blower circulates, and the upstream-side channel, through which air sucked into the blower circulates,
   the first unit has a main channel in which an upstream end is connected to the upstream-side channel and a downstream end is connected to the downstream-side channel, while the first unit is attached to the second unit, and
   a connection point between the main channel and the upstream-side channel, or a connection point between the main channel and the downstream-side channel comprises the cylindrical circulation portion and the connection portion.

2. The CPAP device according to claim 1, wherein
   the first terminal has a first contact surface which extends in a direction crossing an axis orthogonal to an opening plane of the cylindrical circulation portion,
   the second terminal has a second contact surface which faces the first contact surface when an axis orthogonal to an opening plane of the opening is parallel to the axis orthogonal to the opening plane of the cylindrical circulation portion, and the first contact surface is in surface contact with the second contact surface while the first unit is attached to the second unit.

3. The CPAP device according to claim 2, wherein the first terminal is inside an outer peripheral surface of the cylindrical circulation portion in a radial direction.

4. The CPAP device according to claim 2, wherein
either one of the first unit and the second unit comprises a battery,
the other of the first unit and the second unit is electrically connected to the battery via the one of the first terminal and the second terminal while the first unit is attached to the second unit, and
a notification portion which makes a notification when current flow is electrically connected to the first terminal or the second terminal.

5. The CPAP device according to claim 1, wherein the first terminal is inside an outer peripheral surface of the cylindrical circulation portion in a radial direction.

6. The CPAP device according to claim 5, wherein
either one of the first unit and the second unit comprises a battery,
the other of the first unit and the second unit is electrically connected to the battery via the one of the first terminal and the second terminal while the first unit is attached to the second unit, and
a notification portion which makes a notification when current flow is electrically connected to the first terminal or the second terminal.

7. The CPAP device according to claim 1, wherein
the first terminal extends in a circumferential direction on either one of an outer peripheral surface of the cylindrical circulation portion and an inner peripheral surface of the cylindrical circulation portion, and is exposed in a radial direction.

8. The CPAP device according to claim 7, wherein
either one of the first unit and the second unit comprises a battery,
the other of the first unit and the second unit is electrically connected to the battery via the one of the first terminal and the second terminal while the first unit is attached to the second unit, and
a notification portion which makes a notification when current flow is electrically connected to the first terminal or the second terminal.

9. The CPAP device according to claim 1, wherein
either one of the first unit and the second unit comprises a battery,
the other of the first unit and the second unit is electrically connected to the battery via the one of the first terminal and the second terminal while the first unit is attached to the second unit, and
a notification portion which makes a notification when current flow is electrically connected to the first terminal or the second terminal.

* * * * *